(12) United States Patent
Wagner et al.

(10) Patent No.: US 12,702,523 B2
(45) Date of Patent: Aug. 11, 2026

(54) ADJUSTABLE HEADPIECE WITH ANATOMICAL MARKERS AND METHODS OF USE THEREOF

(71) Applicant: Highland Instruments, Somerville, MA (US)

(72) Inventors: Timothy Andrew Wagner, Somerville, MA (US); William Edelman, Sharon, MA (US); Laura Dipietro, Cambridge, MA (US); Paul James Mulhauser, New York, NY (US); Kyungmin Andy Lee, New York, NY (US)

(73) Assignee: Highland Instruments, Inc., Somerville, MA (US)

( * ) Notice: Subject to any disclaimer, the term of this patent is extended or adjusted under 35 U.S.C. 154(b) by 359 days.

(21) Appl. No.: 16/552,929

(22) Filed: Aug. 27, 2019

(65) Prior Publication Data

US 2020/0054414 A1 Feb. 20, 2020

Related U.S. Application Data

(63) Continuation of application No. 15/507,994, filed as application No. PCT/US2015/053142 on Sep. 30, 2015, now abandoned.

(Continued)

(51) Int. Cl.

| | |
|---|---|
| ***A61B 90/00*** | (2016.01) |
| ***A61B 90/50*** | (2016.01) |
| ***A61N 1/04*** | (2006.01) |
| ***A61N 7/00*** | (2006.01) |
| ***F16M 13/04*** | (2006.01) |

(52) U.S. Cl.

CPC ............ *A61B 90/39* (2016.02); *A61N 1/0456* (2013.01); *A61N 1/0472* (2013.01);

(Continued)

(58) Field of Classification Search

None

See application file for complete search history.

(56) References Cited

U.S. PATENT DOCUMENTS 8,603,014 B2 * 12/2013 Alleman .............. A61B 8/4427 601/2
8,613,714 B2 12/2013 Alleman et al.

(Continued)

FOREIGN PATENT DOCUMENTS

| | | | |
|---|---|---|---|
| EP | 3092617 | A1 | 11/2016 |
| WO | 2007138598 | A2 | 12/2007 |
| WO | 2013036337 | A1 | 3/2013 |

OTHER PUBLICATIONS

Teplan. "Fundementals of EEG measurement." Measurement Sci. Rev. 2(2002): 1-11.

*Primary Examiner* — Jonathan Cwern

(74) *Attorney, Agent, or Firm* — Womble Bond Dickinson (US) LLP; Deborah M. Vernon; John V. Forcier

(57) ABSTRACT

The invention generally relates to an adjustable headpiece with anatomical markers and methods of use thereof. In certain embodiments, the invention provides an apparatus that includes a headpiece configured to be worn on a head of a user. The headpiece includes at least a first receptacle configured to receive and retain a first energy source, and the headpiece is adjustable in at least one direction. There is at least one anatomical marker coupled to the headpiece. In that manner, a position of the receptacle can be adjustably aligned to a region of neural tissue in the head based on an alignment of the at least one anatomical marker with its designated anatomical structure.

21 Claims, 12 Drawing Sheets

Related U.S. Application Data

(60) Provisional application No. 62/069,476, filed on Oct. 28, 2014.

(52) U.S. Cl.
CPC ............. *A61N 1/0484* (2013.01); *A61N 7/00* (2013.01); *F16M 13/04* (2013.01); *A61B 2090/3937* (2016.02); *A61B 2090/502* (2016.02); *A61N 2007/0021* (2013.01); *A61N 2007/0026* (2013.01)

(56) References Cited

U.S. PATENT DOCUMENTS 8,718,758 B2 5/2014 Wagner et al.
8,805,548 B2 * 8/2014 Mignolet ............. A61N 1/0484 607/139
9,020,576 B2 * 4/2015 Nagatani .................. A61B 5/05 600/407
2004/0249271 A1 * 12/2004 Besson ................ A61B 6/5247 600/437
2005/0124897 A1 * 6/2005 Chopra .................... A61N 7/00 600/459
2008/0046053 A1 2/2008 Wagner et al.
2010/0152810 A1 6/2010 Minogue et al.
2011/0275927 A1 11/2011 Wagner et al.
2012/0083717 A1 4/2012 Alleman et al.
2012/0226200 A1 9/2012 Wagner et al.
2013/0184728 A1 * 7/2013 Mishelevich ............ A61N 7/00 606/169
2015/0018667 A1 * 1/2015 Radman ................. A61B 5/389 607/45

* cited by examiner

ADJUSTABLE HEADPIECE WITH ANATOMICAL MARKERS AND METHODS OF USE THEREOF

RELATED APPLICATION

The present application is a continuation of U.S. application Ser. No. 15/507,994, filed Mar. 1, 2017, which is a 35 U.S.C. § 371 national phase application and claims the benefit of and priority to PCT/US15/53142, filed Sep. 30, 2015, which claims the benefit of and priority to U.S. provisional application Ser. No. 62/069,476, filed Oct. 28, 2014, the content of each of which is incorporated by reference herein in its entirety.

GOVERNMENT SUPPORT

This invention was made with Government support under Grant Number 5R44NS080632 awarded by the National Institute of Neurological Diseases and Stroke (NINDS) Of the National Institutes of Health (NIH). The Government has certain rights in this invention.

FIELD OF THE INVENTION

The invention generally relates to an adjustable headpiece with anatomical markers and methods of use thereof.

BACKGROUND

There has been a rapid increase in the application of stimulation devices to treat a variety of pathologies, particularly neuropathologies. FDA approved therapies already include treatments for disorders such as Parkinson's disease, depression, and epilepsy, and the number of indications being explored is growing exponentially. Effective electromagnetic stimulation techniques alter the firing patterns of cells by applying electromagnetic energy to electrically responsive cells, such as neural cells. The stimulation may be applied invasively, e.g., by performing surgery to remove a portion of the skull and implanting electrodes in a specific location within brain tissue, or non-invasively, e.g., transcranial direct current stimulation or transcranial magnetic stimulation. Other forms of energy can also be used to stimulate tissue, both invasively and noninvasively.

Non-invasive stimulation requires that the stimulation source be precisely positioned on the scalp so that the stimulation can be focused on a particular structure or structures in the brain. Traditionally, trial and error was used until the desired response (finger twitch) was generated. That process involved moving the non-invasive stimulation source along the head until the stimulation source stimulated the structure in the brain that caused the desired response. For example, a finger twitch indicated that the stimulation source was positioned to stimulate the motor cortex. In another approach, a non-invasive stimulation source is positioned over the head using external landmarks and measurements. That process involves a technician using a tape measure to measure from an external landmark on a subject's head to the desired location on the head that corresponds with where the particular structure within the brain is located. The measuring process is repeated from different markers to get a precise location for placement of the stimulation source. The measuring approach is not only cumbersome, it also requires that a subject be re-measured every time they come in for treatment.

More recently, imaging sources have been used to facilitate positioning of the stimulation source. In that approach, the non-invasive stimulation source is navigated and positioned over a specified target location based upon feedback from the imaging source, such as a subject's MRI image. However, it is costly to use imaging data to facilitate placement of the stimulation source, and requires a technician to have access to expensive imaging instruments, such as an MRI machine. Furthermore, reliance on imaging data for positioning of the stimulation source means that a subject must always come to a physician's office for stimulation.

SUMMARY

The invention provides a stimulation apparatus that is custom fit to a user's head and that allows for stimulation to be effectively targeted (localized) to a desired region of neural tissue. Aspects of the invention are accomplished using a headpiece configured to be worn on a head of a user. The headpiece includes at least a first receptacle configured to receive and retain a first energy source, and the headpiece is adjustable in at least one direction. There is at least one anatomical marker coupled to the headpiece. The apparatus is configured such that a position of the receptacle can be adjustably aligned to a region of neural tissue in the head based on an alignment of the at least one anatomical marker with its designated anatomical structure. Once the proper alignment is achieved, the configuration of the headpiece is locked in place. Accordingly, the apparatus is customized to a subject's head and repeatably and reliably positions a non-invasive stimulation source at a proper location on the subject's head for stimulation of a particular brain structure. In that manner, a subject does not need to be re-measured for each stimulation session, because the apparatus has been custom fit to the user's head. That saves the subject time during subsequent stimulation sessions and the reproducibility of the targeting makes it easy to effectively dose the stimulation and characterize safety parameters. Furthermore, once custom fit, imaging data is not required for positioning of the stimulation source in subsequent stimulation sessions, so the subject can receive stimulation outside of a physician's office.

In certain embodiments, the apparatus includes the first energy source that is configured to connect to the receptacle. The connection may be a permanent connection or a releasable connection.

Another aspect of the invention provides an apparatus that includes a headpiece configured to be worn on a head of a user. The headpiece includes a first energy source, and the headpiece is adjustable in at least one direction. At least one anatomical marker is coupled to the headpiece so that a position of the first energy source can be adjustably aligned to a region of neural tissue in the head based on an alignment of the at least one anatomical marker with its designated anatomical structure.

For either of the above aspects, the apparatuses may additionally include a locking mechanism that locks adjustability of the headpiece to prevent further adjustment of the headpiece while the apparatus is being worn on the head of the user. Generally, the headpiece is adjustable in a plurality of different directions. For example, the headpiece is adjustable in at least a vertical direction and/or a horizontal direction.

Positioning of the first energy source may be accomplished using only a single anatomical marker. However, for either of the above aspects, the apparatuses may include a plurality of anatomical markers, each marker being coupled to the headpiece. The markers can be located about the headpiece in any configuration and at any angle to one another. In certain embodiments, at least two of the markers are arranged about the headpiece to be perpendicular to each other. In other embodiments, at least two of the markers are arranged about the headpiece to be 180 degrees with respect to each other. In certain embodiments, the markers are configured such that at least two of the markers are arranged about the headpiece to be perpendicular to each other, and at least two of the markers are arranged about the headpiece to be 180 degrees with respect to each other. More than one marker may be advantageous over a single marker embodiment because it may allow for more accurate positioning of the stimulation sources. In a preferred embodiment, three or more markers are used so that the stimulation sources may be triangulated for precise locating, based on the three markers.

Stimulation can be achieved with only a single energy source. However, for either of the above aspects, more than one energy source may be used to achieve stimulation of the neural tissue. In that manner, apparatuses of the invention may include a second receptacle for a second energy source, or more than two receptacles and/or energy sources.

Any type of energy sources known in the art may be used with apparatuses of the invention. Exemplary types of energy sources include mechanical, optical, electromagnetic, thermal, or a combination thereof. In particular embodiments, the energy source is a mechanical source, such as an ultrasound device. In other embodiments, the energy source is an electrical source. In other embodiments, the energy source is a magnetic source. Other exemplary types of energy sources include Transcranial Direct Current Stimulation (TDCS), Transcranial Ultrasound (TUS), Transcranial Doppler Ultrasound (TDUS), Transcranial Electrical Stimulation (TES), Transcranial Alternating Current Stimulation (TACS), Cranial Electrical Stimulation (CES), or Transcranial Magnetic Stimulation (TMS). In other embodiments, the stimulation is provided by a combination of two energy sources, such as an electric source and a mechanical source. In other embodiments, the stimulation is a combination of Transcranial Ultrasound (TUS) and Transcranial Direct Current Stimulation (TDCS).

Another aspect of the invention provides an apparatus that includes a headpiece configured to be worn on a head of a user. The headpiece includes a first receptacle configured to receive and retain a first energy source and a second receptacle configured to receive and retain a second energy source, and the headpiece is adjustable in a plurality of different directions. At least three anatomical markers are coupled to the headpiece, in which a first anatomical marker is a nasion marker, a second anatomical marker is an inion marker, and a third anatomical marker is a first tragus marker. The apparatus is configured so that a position of at least one of the receptacles can be adjustably aligned relative to a region of neural tissue in the head based on an alignment of the at least three anatomical markers with their designated anatomical structures. In certain embodiments, the apparatus includes the first and second energy sources, and any of the above sources may be used with this aspect of the invention. The first and second energy sources are configured to connect to the receptacle. The connection may be a permanent connection or a releasable connection. In certain embodiments, the first receptacle is adjustably coupled to the headpiece and the second receptacle is non-adjustably coupled to the headpiece.

In certain embodiments, the apparatus further includes a fourth anatomical marker, such as a second tragus marker. In such embodiments, the first tragus marker aligns to one side of the head and the second tragus marker aligns to the other side of the head. In other embodiments, the apparatus further includes a fifth anatomical marker, such as a CZ marker. In certain embodiments, the apparatus additionally includes a locking mechanism that locks adjustability of the headpiece to prevent further adjustment of the headpiece while the apparatus is being worn on the head of the user.

DETAILED DESCRIPTION

Figure 1:
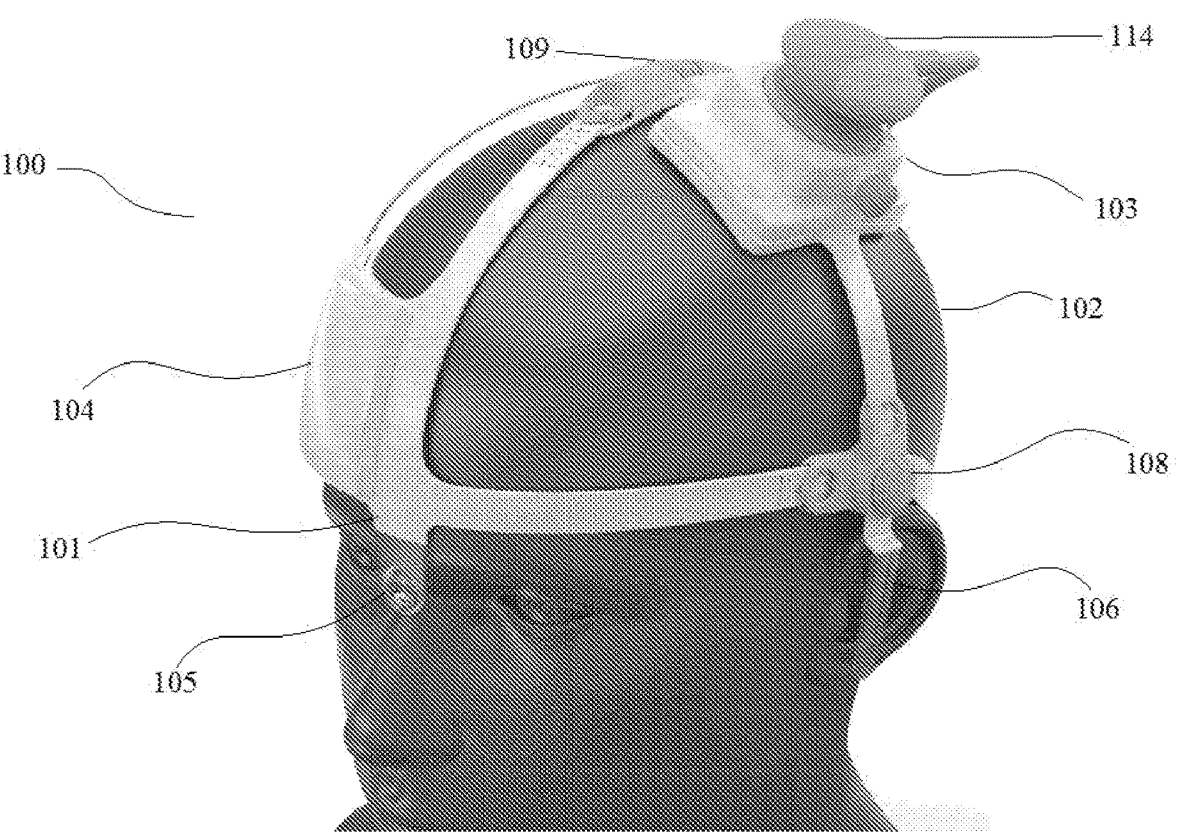
FIG. 1 is an illustration of an embodiment of an apparatus of the invention from a right side perspective.
Figure 2:
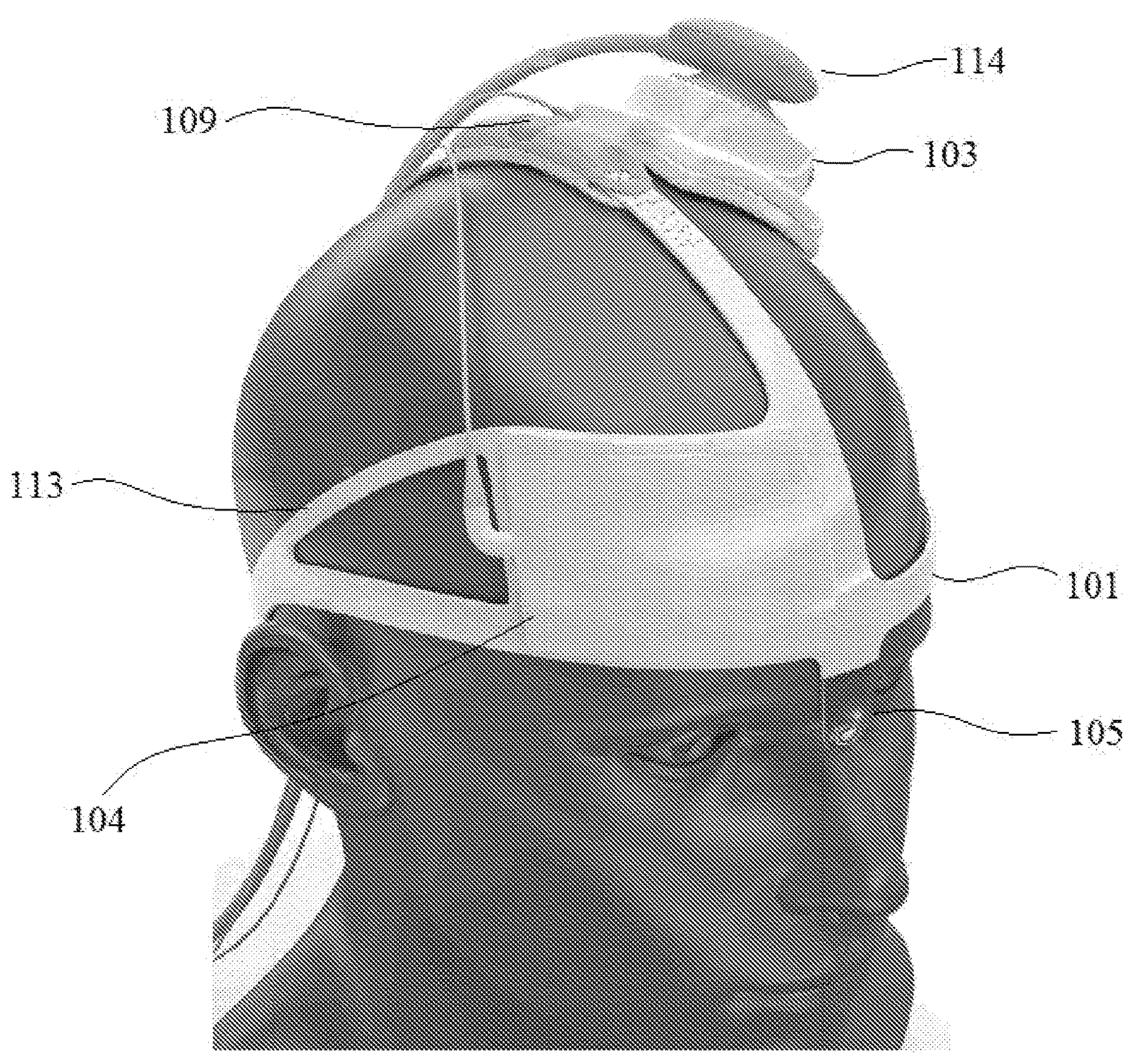
FIG. 2 is an illustration of the embodiment of the apparatus shown in FIG. 1 from a left side perspective.
Figure 3:
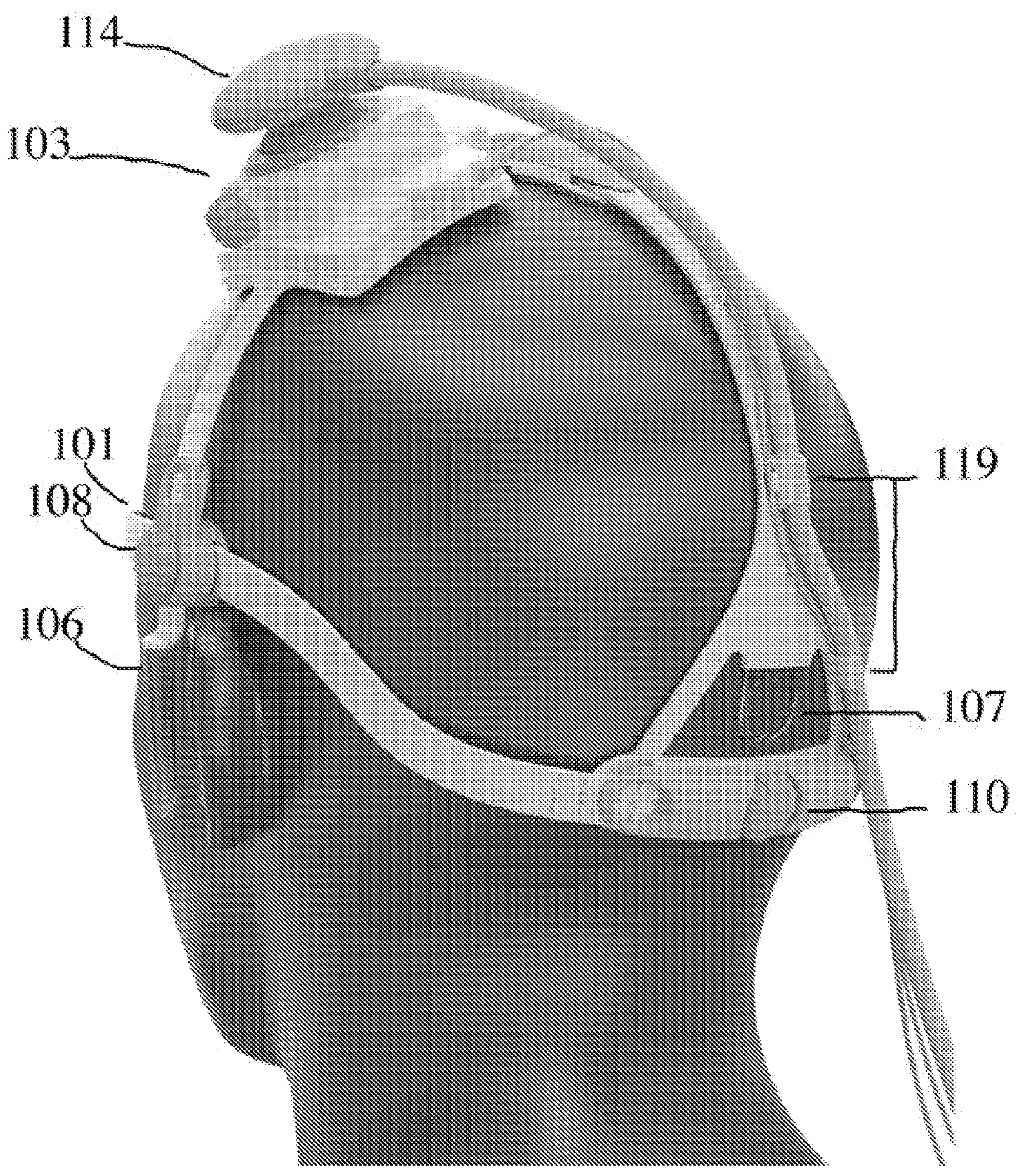
FIG. 3 is an illustration of the embodiment of the apparatus shown in FIG. 1 from a rear perspective.

The invention generally relates to an adjustable headpiece with anatomical markers and methods of use thereof. An exemplary embodiment of an apparatus of the invention is shown in FIGS. 1-3, which show an apparatus 100 that includes a headpiece 101 configured to be worn on a head 102 of a user. FIG. 1 illustrates the apparatus from the right side, FIG. 2 illustrates the apparatus from the left side, and FIG. 3 illustrates the apparatus from a rear view. The headpiece 101 can be made of any material, such as metal, ceramics, rubber, foam, fabrics, composite material, and/or plastic. In certain embodiments, the material is foam or plastic and the headpiece is formed by injection molding the components to produce the headpiece. In certain embodiments the material is a plastic that can be die cut from a sheet. In certain embodiments the parts are printed using a 3D printer. Any form of manufacture may be used, such as those described in Fundamentals of Composites Manufacturing: Materials, Methods and Applications, Second Edition by A. Brent Strong (published Nov. 27, 2007); Manufacturing Process Selection Handbook: From design to manufacture by K. G. Swift and J. D Booker (published Feb. 15, 2013); and Fundamentals of Modern Manufacturing: Materials, Processes, and Systems by M. Groover (published Jan. 5, 2010) the references which are incorporated herein in their entirety. The headpiece 101 shown in FIGS. 1-3 is only exemplary, and headpieces of the invention do not need to have the specific configuration shown in FIGS. 1-3. Any configuration is within the scope of the invention so long as the headpiece 101 is configured to be worn on the user's head 102. For example, the headpiece 101 can have more or fewer cross-connecting pieces. For example, FIGS. 1-3 show headpiece 101 having an additional support connector 113. Such connector is optional, and embodiments of the invention can include more or fewer support connectors, depending on the stimulation sources and/or anatomical markers being used. The headpiece 101 can be a full cap or helmet. Generally, the configuration of the headpiece 101 will be dependent on the number of stimulation sources and the number of anatomical markers.

As shown in FIGS. 1-3, headpiece 101 has two receptacles 103 and 104 for two stimulation sources. FIGS. 1-3 show apparatus 100 with the two stimulation sources coupled to the receptacles 103 and 104. The coupling between the receptacles 103 and 104 can be a removable coupling or can be a permanent coupling. Each receptacle can be independently configured. For example, one receptacle can have a permanent coupling with one stimulation source and the other receptacle can have a removable coupling with the other energy source. Alternatively, each receptacle can be identically configured, e.g., both with permanent couplings, both with removable couplings. As another example, one receptacle could be adjustable in position and the other fixed in position on the headpiece.

As will be discussed in other embodiments below, two stimulation sources is only exemplary, and apparatuses of the invention require only a single stimulation source, but can include more than one stimulation source, such as two, three, four, five, etc. stimulation sources. In the exemplary embodiment shown in FIGS. 1-3, there is a first receptacle 103 for a first stimulation source and part of the second stimulation source and a second receptacle 104 for the other part of the second stimulation source. The position of receptacles 103 and 104 is only exemplary. In FIGS. 1-3, the receptacles are illustratively positioned to show a configuration for stimulating the motor cortex. The positioning of the receptacles 103 and 104 depends on the target for stimulation. Exemplary targets include dorsal lateral prefrontal cortex, any component of the basal ganglia, nucleus accumbens, gastric nuclei, brainstem, thalamus, inferior colliculus, superior colliculus, periaqueductal gray, primary motor cortex, supplementary motor cortex, occipital lobe, Brodmann areas 1-48, primary sensory cortex, primary visual cortex, primary auditory cortex, amygdala, hippocampus, cochlea, cranial nerves, cerebellum, frontal lobe, occipital lobe, temporal lobe, parietal lobe, or sub-cortical structures.

Figure 8:
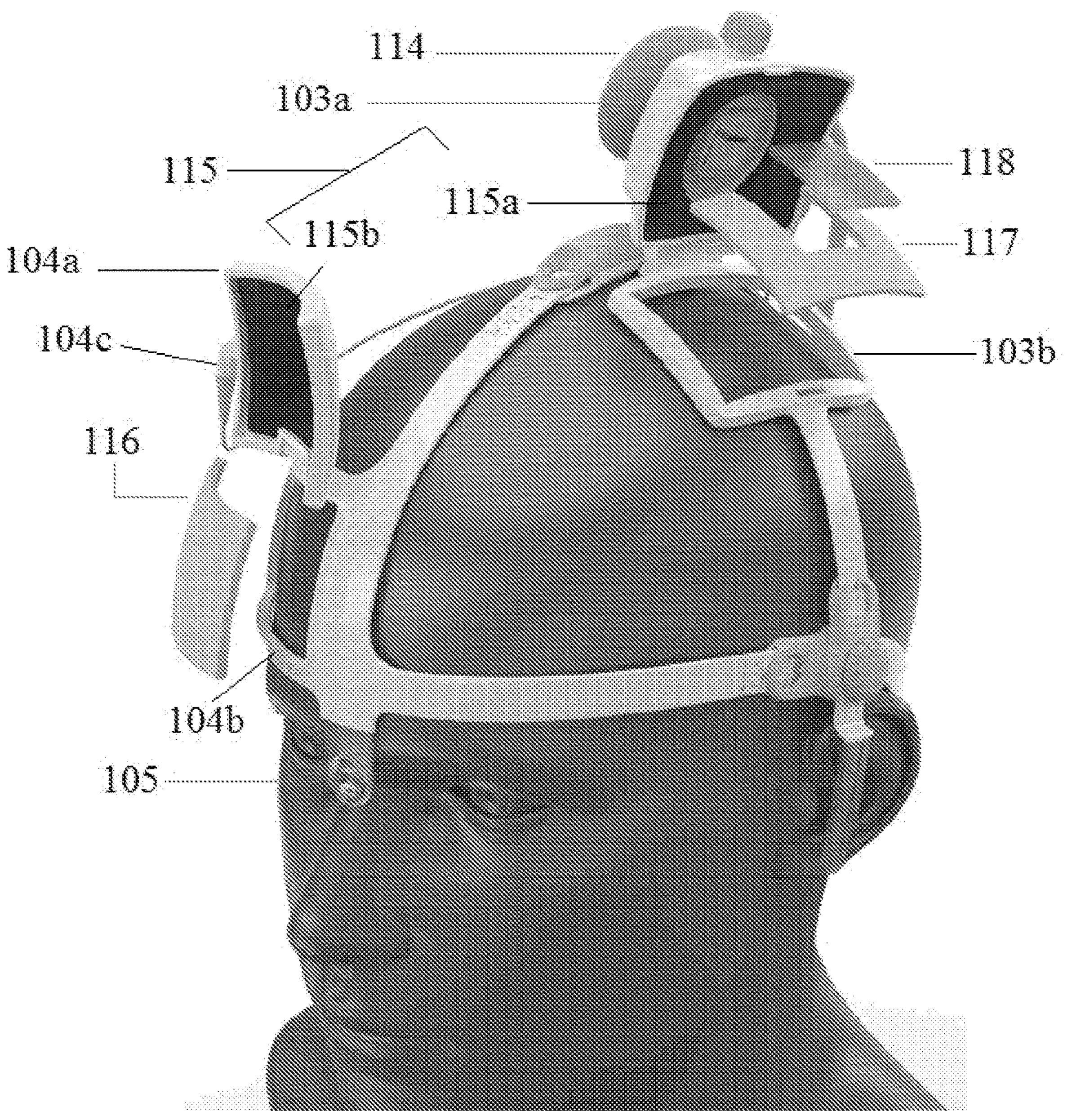
FIG. 8 is an illustration of the embodiment of the apparatus shown in FIG. 1, showing details regarding receptacles and stimulation sources used in the apparatus of the invention.

Receptacles 103 and 104 shown in FIGS. 1-3 are only exemplary, and other configurations for the receptacles are within the scope of the invention. FIG. 8 provides greater detail regarding the receptacles and the stimulation sources. Receptacle 103 is hingedly connected to headpiece 101. That connection is an exemplary connection and is not meant to be limiting of the invention. Connections other than hinged connections can be used with receptacle 103. Receptacle 103 include a first stimulation source 114, and a first portion 115*a* of a second stimulation source 115. As shown in FIG. 8, the first portion 115*a* of the second stimulation source 115 is a conductive electrode pad. The electrode pad can be permanently or removably coupled to an inside of receptacle 103. In this embodiment, it is coupled to an inside of the hinged cover 103*a*. As shown in FIG. 8, first stimulation source 114 is an ultrasound probe that may be permanently or removably coupled to receptacle 103. In other embodiments multiple stimulation sources can be combined in a single piece, such as a combined ultrasound and electrical stimulation source that could share the same transducer face, and which could be permanently or removably coupled to a receptacle. In certain embodiments the stimulation source could be coupled inside, outside, and/or to part of the receptacle, in whole or part.

Figure 9:
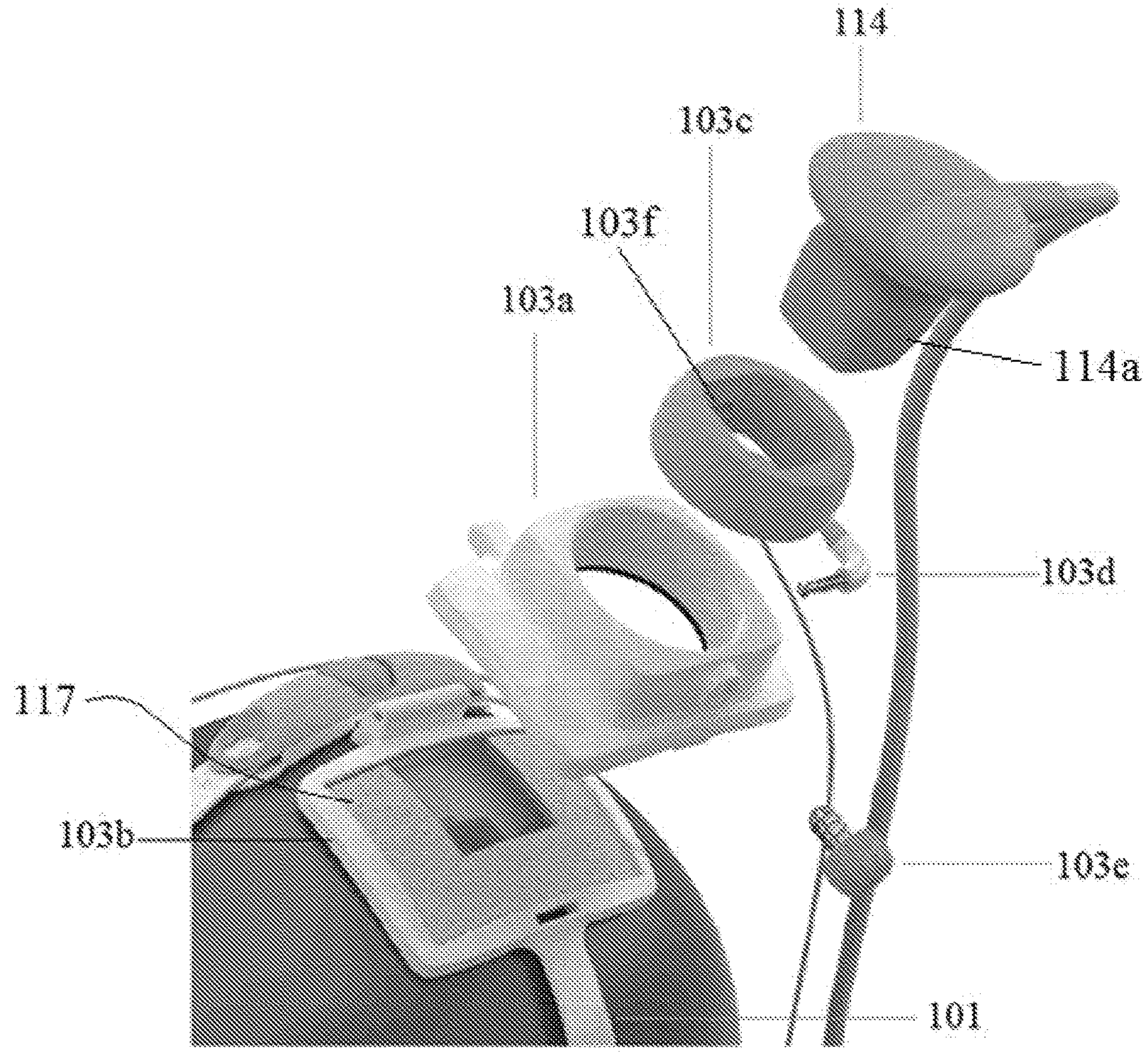
FIG. 9 is an illustration of the embodiment of the apparatus shown in FIG. 1, showing an exploded view of the receptacle on the top of the headpiece shown in FIG. 1.

FIG. 9 shows an exploded view of receptacle 103, which provides a top down view of receptacle 103 without the ultrasound probe coupled thereto. Receptacle 103 includes hinged cover 103*a* that couples to bottom portion 103*b*. Receptacle 103*a* includes a hollow portion and a micro adjust ball joint 103*c* sits within the hollow portion. The micro adjust ball joint 103*c* includes a hollow portion so that the first stimulation source 114 (e.g., an ultrasound probe) can sit within the micro adjust ball joint 103*c*. The micro adjust ball joint 103*c* allows for fine tune adjustment of the position of the first stimulation source 114 (e.g., an ultrasound probe). The micro adjust ball joint 103*c* can also be coupled to the receptacle such that it has a freedom of movement in depth so further adjustment of the ultrasound transducer positioning can be accomplished (i.e., it has a full range of movement in all directions). An electrode connector 103*d* is coupled to the hinged cover 103*a* component to provide an operable connection to the first portion 115*a* of the second stimulation source 115 (e.g., electrode pad). The electrode connector 103*d* can couple to any location on the receptacle 103 through any type of terminal or mechanism such that it makes contact directly, or through other materials keeping the electrical connection continuous, and for example connect via any type of electrical connection mechanism such as a USB connection, a connection from a phone (such as a connector for an Apple mobile phone), a connection from a computer or electronic device, a headphone jack (e.g., a 2.5 mm or 3.5 mm mono or stereo connector), a plug and socket connector, a crimp on connector, a blade connector, a banana connector, a DC connector, a D-subminiature connectors, an Ethernet connector, a BNC connector, and optical cable, a phone connector, and/or an alligator connector. The electrical connection can also be made through a telecommunications device (for example in an alternative embodiment an electrical power source is housed in the receptacle, which could include some internal control electronics, and be controlled through a telecommunications connection), such as BLUETOOTH (wireless technology standard for exchanging data over short distances using short-wavelength UHF radio waves in the ISM band from 2.4 to 2.485 GHz), a Wi-Fi connection (a local area wireless technology that allows an electronic device to exchange data or connect to the internet using 2.4 GHz UHF and 5 GHz SHF radio waves, and further described as a wireless local area network (WLAN) products that are based on the Institute of Electrical and Electronics Engineers' (IEEE) 802.11 standards), mobile phone standards such as 2G, 3G, 4G or LTE, fixed wireless connections, and/or any other wireless connection. In certain embodiments the device might include code, circuitry, and/or computational components to allow someone to secure (e.g., encrypt, password protect, scramble, etc.) the data being sent between the components in the headpiece and an external device via the telecommunications equipment. The code, circuitry, and/or computational components can be designed to match with external source and/or headpiece controllers. Code, circuitry, and/or computational components can also be used to secure patient data and/or operational code stored in the headpiece or in external communication. In certain embodiments, the receptacle 103 includes safety components operably coupled to the stimulation source. Exemplary safety components include components for checking stimulation intensity and/or duration. Exemplary safety components are described for example in Brocke (U.S. Pat. No. 8,554,324), the content of which is incorporated by reference herein in its entirety. Furthermore in certain embodiments, safety components, such as those to control the stimulation, make stimulation inoperable, and/or those that measure the characteristics of stimulation such as through transducers, such as based on assessments of temperature, conductivity, bridging medium properties, or properties of the scalp and/or scalp connection can be housed in the receptacle.

The electrode connector 103*d* can be removable and replaceable, or permanently fixed. A tightening knob 103*e* connects to the hinged cover 103*a* and locks the micro adjust ball joint 103*c* in place in the receptacle 103. The micro adjust positioning system can be adjusted and then fixed with any fixing mechanism, such as a screw mechanism, either for use during a single use, multiple uses, or permanently. When not permanently fixed, the system could be adjusted again later through the same process for additional use such as for example at a different location and/or for a different subject. The first stimulation source 114 (e.g., an ultrasound probe) can be fixed to the micro adjust ball through connector mechanism 103*f* which may or may not be releasable. By having a separate fixing mechanism for the micro adjust ball 103*c* and the first stimulation source 114 (e.g., an ultrasound probe), one could have the ability to fix the position of the micro adjust ball 103*c*, and thus the stimulation source, and keep that position fixed while still being able to remove the first stimulation source from the receptacle 103. This for example could allow a care provider to tune the device fitting for a patient by locking the micro adjust positioning system and still being able to remove and exactly replace the first stimulation source 114. In an alternate embodiment, a tightening apparatus could be used to fix both the micro adjust ball and the first stimulation source. In an alternate embodiment, the micro adjust ball 103*c* is not used, and the ultrasound source is fit to a fixed component of the receptacle. In alternate embodiments, the first stimulation source 114 and the parts of the receptacle that connect to it are not used in receptacle 103, and only the second stimulation source 115 is used.

Additionally, stimulation source 114 (e.g., an ultrasound probe), can include a connector mechanism 114*a* that interacts with connector mechanism 103*f* to secure stimulation source 114 to receptacle 103. For example, connector mechanism 103*f* is an indentation and connector mechanism 114*a* is a corresponding protrusion. The protrusion couples into the indentation, thereby locking the stimulation source 114 into place. The locking can be permanent or releasable.

Turning back to FIG. 8, receptacle 104 is hingedly connected to headpiece 101, having a hinged cover 104*a* and a bottom portion 104*b*. That connection is an exemplary connection and is not meant to be limiting of the invention. Connections other than hinged connections can be used with receptacle 104 such as for example the component can be permanently fixed and/or continuous with the headpiece 101. Receptacle 104 includes a second portion 115*b* of a second stimulation source stimulation 115. As shown in FIG. 8, the second portion 115*b* of the second stimulation source 115 is a conductive electrode pad. The electrode pad can be permanently or removably coupled to an inside of receptacle 104. In this embodiment, it is coupled to an inside of the hinged cover 104*a*. Receptacle 104 includes an electrode connector 104*c* to provide an operable connection to the second portion 115*b* of the second stimulation source 115 (e.g., electrode pad) within the receptacle 104. In alternate embodiments, receptacle 104 is not included as part of the headpiece 101, and just receptacle 103 is included, such that the electric source 115, is mono-polar and just makes use of stimulation source 115*a*. With a mono-polar application, based on an electric source, a ground electrode may be placed on the body of the patient to be stimulated which could be independent of the headpiece, but coupled through stimulation source circuitry.

As shown in FIG. 3, the headpiece 101 can include securing features 119, such as clips, to secure wires that extend from the receptacles 103 and/or 104 and/or energy sources 114 and/or 115.

Bridging mediums can be used in connect with one or both stimulation/energy sources. Any bridging medium known in the art can be used with apparatuses of the invention and the bridging medium chosen will depend on the type of stimulation/energy source used. Bridging mediums and their use are further described for example in Wagner et al. (U.S. Pat. No. 8,718,758), the content of which is incorporated by reference herein in its entirety. FIG. 8 shows that a bridging medium is used with both energy sources. In receptacle 104 there is only a single bridging medium 116. The bridging medium used is based on the type of stimulation/energy source being used in the receptacle. In the embodiment shown in FIG. 8, the second portion 115*b* of the second stimulation source 115 is a conductive electrode pad. Accordingly, the bridging medium 116 based on this type of stimulation/energy source is a conductive sponge, such as simple sponge soaked with saline. A bridging medium, in whole or in part, may be permanently or removably coupled to either or both of the receptacles 103 and 104. The bridging medium may be contained in a separate receptacle (e.g., a receptacle within the receptacle) so that the bridging medium does not make contact with the patient's head (such as for example containing the edges of a saline soaked sponge with a rubber sealing material) or other components of the apparatus.

In receptacle 104 there are two different bridging mediums 117-118. In the embodiment shown in FIG. 8, the first portion 115*a* of the second stimulation source 115 is a conductive electrode pad and the first stimulation source 114 is an ultrasound probe. Accordingly, the bridging medium 117 used in connection with the first portion 115*a* of the second stimulation source 115 is a conductive sponge. The bridging medium 118 used in connection with the first stimulation source 114 is a conductive gel pad, where the gel pad can conduct electrical energy (such as for example from the second stimulation source) and simultaneously allow ultrasonic energy transmission through the material. The pad may further be coupled to the skin with an ultrasonic gel and/or fluid. In an alternative embodiment, one component could serve as the only bridging medium for both sources. In alternative embodiments, the receptacle may for instance contain a fluid and/or gel bridging material.

The descriptions above regarding the receptacles and stimulation/energy sources is only exemplary. Any type of stimulation source (i.e., energy source) known in the art may be used with apparatuses of the invention. Exemplary types of energy sources include mechanical, optical, electromagnetic, thermal, or a combination thereof. In particular embodiments, the energy source is a mechanical source, such as an ultrasound device. In other embodiments, the energy source is an electrical source. In other embodiments, the energy source is a magnetic source. Other exemplary types of energy sources include Transcranial Direct Current Stimulation (TDCS), Transcranial Ultrasound (TUS), Transcranial Doppler Ultrasound (TDUS), Transcranial Electrical Stimulation (TES), Transcranial Alternating Current Stimulation (TACS), Cranial Electrical Stimulation (CES), Transcranial Pulsed Stimulation, or Transcranial Magnetic Stimulation (TMS). In other embodiments, the stimulation is provided by a combination of two energy sources, such as an electric source and a mechanical source. In other embodiments, the stimulation is a combination of Transcranial Ultrasound (TUS) and Transcranial Direct Current Stimulation (TDCS).

In the embodiment shown in FIGS. 1-3, energy source 114 is a transcranial ultrasound source (TUS) and energy source 115 is a Transcranial Electrical Stimulation (TES). The types and strengths of the fields provided by each source and the manner of providing those fields (e.g., pulsed, constant (i.e., time invariant)) is described for example in Wagner et al. (U.S. patent application publication number 2008/0046053), the content of which is incorporated by reference herein in its entirety. Energy sources 114 and 115 and/or receptacles 103 and 104 or are oriented with respect to each other such that the energy fields produced by the sources overlap with each at the target location. For example, in FIG. 1, the first stimulation source 114 is oriented with respect to the second stimulation source 115 such that an energy field produced by the first stimulation source 114 intersects the energy produced by the second stimulation source 115 at the target region of neural tissue in the head, in this case, the motor cortex, in the case when both stimulation sources are operating at the same time. In alternative embodiments, the headpiece and/or subcomponents can also be used with stimulation sources operating independently and/or designed so just one of the stimulation sources is included in the system.

Headpiece 101 includes at least three anatomical markers. As discussed below, three anatomical markers is only exemplary, and apparatuses of the invention can have only a single anatomical marker, or can have more than one anatomical marker, such as two, three, four, five, six, seven, eight, nine, ten, etc. The apparatus shown in FIGS. 1-3 has three anatomical markers. FIG. 1 shows two of the anatomical markers and FIG. 2 shows the third anatomical marker. FIG. 3 illustrates that there is no anatomical marker on the right side of the device in this embodiment. Anatomical marker 105 is a nasion marker (FIG. 1), anatomical marker 106 is a tragus marker (FIG. 1), and anatomical marker 107 is an inion marker (FIG. 3). Alignment of the different markers with their designated anatomical structures results in proper positioning of the energy sources. In the exemplary embodiment shown in FIGS. 1-3, alignment of nasion marker 105 over the nasion, the tragus marker 106 over the tragus, and the inion marker 107 over the inion, results in energy sources 103 and 104 being positioned on the head such that the energy fields produced by energy sources 103 and 104 intersect at the region of target neural tissue, in this example, the motor cortex. The anatomical markers can be made out of any material or materials, such as for example a thin plastic or rubber which allows an operator to feel the anatomical locations through the materials, such as could provide further confirmation of the device placement. The anatomical markers could also have a location that was hollowed out to allow an operator to directly feel the anatomical location below the marker.

The anatomical markers shown in FIGS. 1-3 are merely illustrative, and other anatomical marks can be used with apparatuses of the invention. Exemplary other anatomical markers include fixed spots along the skull such as the CZ (aka vertex), left temple, right temple, left temple, left orbital, right orbital, immovable top border of the temporomandibular joint, left ear canal, right ear canal, left pre-auriciular point, upper tooth or teeth, right pre-auriciular point, zygomatic arch, fixed skull bones, skull fontanels, and fixed skull sutures. In an alternative embodiment non fixed locations, such the sub-mandibular center location, left ear, right ear, left ear lobe, right ear lobe, tip of nose, eye brow borders, jaw bone, lower tooth or teeth, and/or jaw bone border markings. Fixed spots provide an advantage in reproducibility across different stimulation sessions, and/or more certain targeting. Non fixed spots can be used as an alternative or in combination with fixed spots, but stability of the non-fixed spots is necessary to assure appropriate targeting or reproducibility (often in terms of stable condition relative to other locations), and extra procedures may be required to assure that the non-fixed spots are providing reproducible placement (such as confirming placement with an imaging modality and/or artificially fixing one of the non fixed spots).

Figure 4:
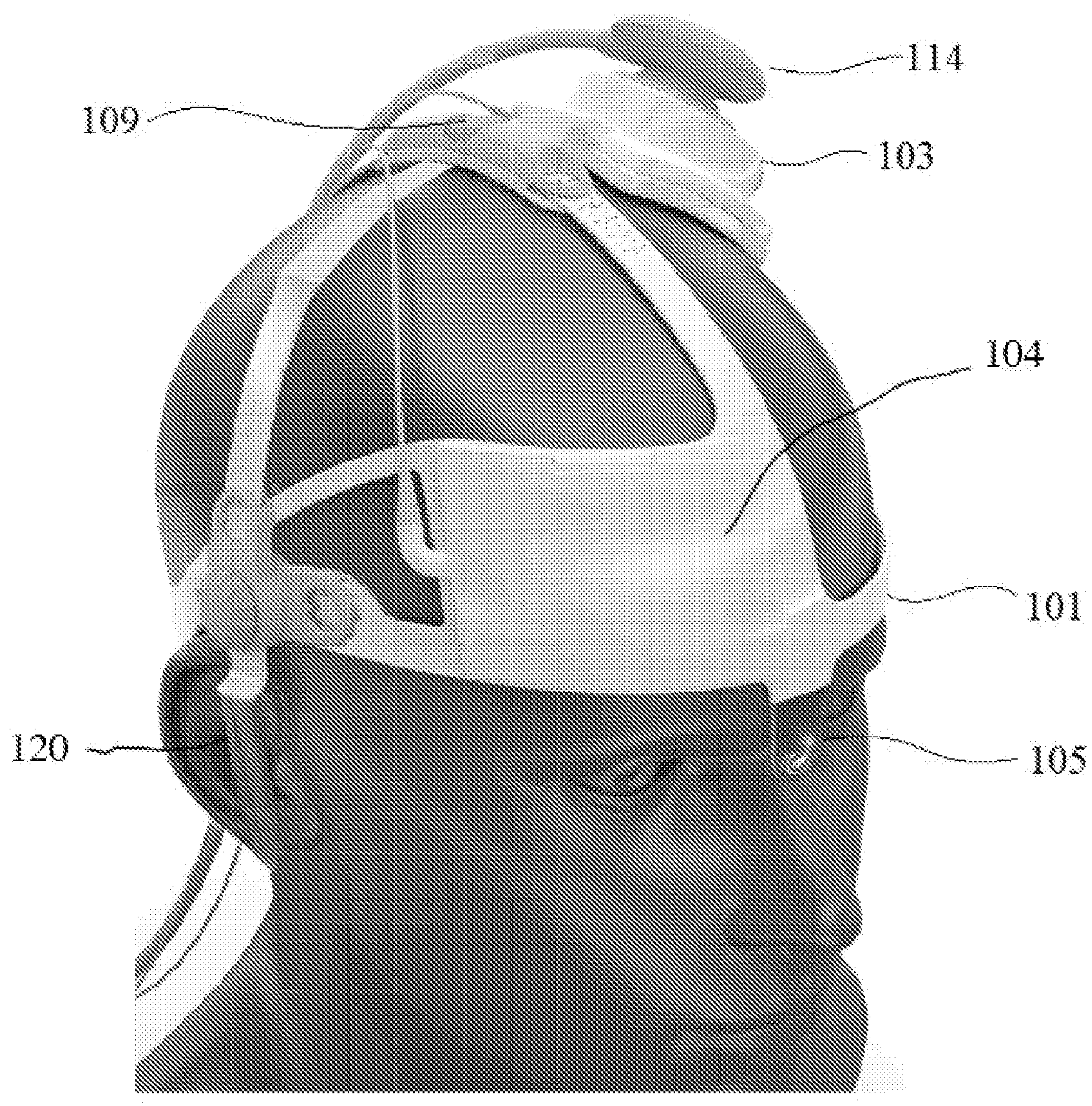
FIG. 4 is an illustration of an embodiment of an apparatus of the invention having four anatomical markers, nasion, inion, and 2 tragus markers.
Figure 5:
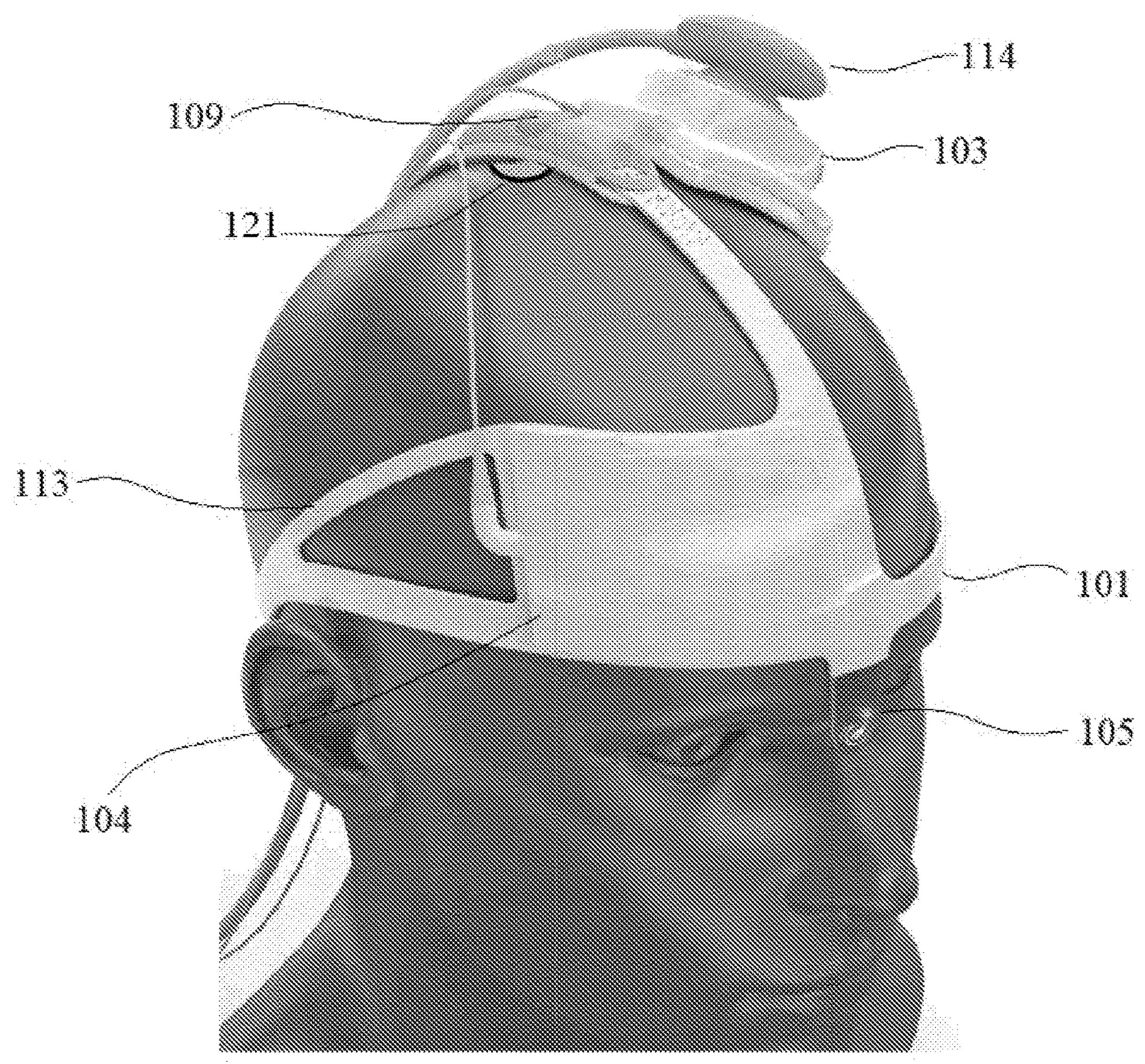
FIG. 5 is an illustration of an embodiment of an apparatus of the invention having four anatomical markers, nasion, inion, tragus, and CZ markers.
Figure 6:
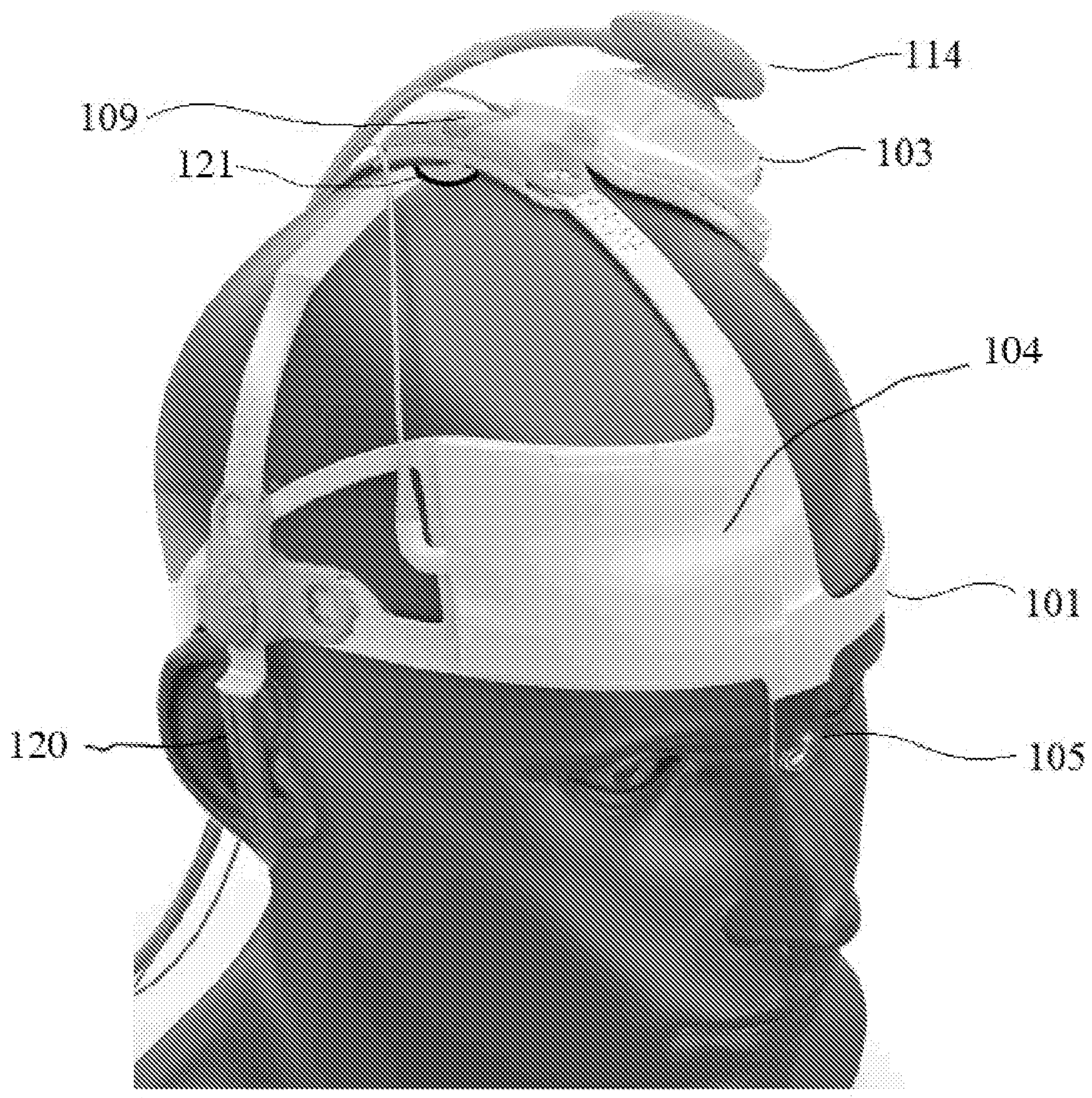
FIG. 6 is an illustration of an embodiment of an apparatus of the invention having five anatomical markers, nasion, inion, 2 tragus, and CZ markers.

Additionally, apparatuses of the invention can use less than three or more than three anatomical markers. For example, the fixation of the headpiece based on the 3 anatomical markers, and fixed angles of components of the headpiece, it can be assumed that the tragus on the left side of the head is symmetrical with the tragus on the right side of the head (FIGS. 1-3). Accordingly, apparatuses of the invention can function using a single tragus marker, on either the left or the right side of the head (FIGS. 1 and 4). However, in certain embodiments, such as for example when not dealing with a symmetric head, apparatuses of the invention include a fourth anatomical marker, such as a second tragus marker 120 (FIG. 4). In other embodiments, apparatuses of the invention include a CZ marker. In certain embodiments, the CZ marker 121 is the fourth anatomical marker, so the apparatus includes a nasion marker 105, an inion marker 107, a tragus marker 106, and a CZ marker 121 (FIGS. 1, 3, and 5). In other embodiments, the CZ marker is the fifth anatomical marker, so the apparatus includes a nasion marker 105, an inion marker 107, two tragus markers 106 and 120, and a CZ marker 121 (FIGS. 1, 3, and 6).

In certain embodiments, the placement of the anatomical marker(s), or other connected components of the headpiece, are controlled by mathematical functions which are used to determine relative or fixed positions of other components, such as based on predetermined relative or fixed angles or distances (such as for example moving a component of the device along 20% along a line defined from the tragus to CZ at the midline between inion and nasion). While this information is preferably determined directly based on marker position and patient head characteristics, other information such as imaging and physiological measurements can be used as part of these mathematical functions. Furthermore, in alternative embodiments a separate marker could be placed as a mathematical function based on the characteristics of the anatomical markers.

More than one marker can be advantageous over a single marker embodiment because it may allow for more accurate positioning of the stimulation sources (and important when using a stimulation source that is not mono-polar, or requires information about the position, angle, and relative placement of a source). In a preferred embodiment, three or more markers are used so that the stimulation sources may be triangulated for precise locating, based on the three markers. In an alternative design four markers or more may be used. A system based on three markers or more markers is important to define a unique and reproducible coordinate system on a patients head that is receiving stimulation (although 4 points is better to define a unique 3 dimensional space, an exemplary headpiece described herein uses the fixed angles of the head piece and the fitting procedure to define a reproducible coordinate space on the stimulation subject's head (for example, by using the headpiece described in FIGS. 1-3, and making use of the locking mechanisms as described herein, 3 orthogonal vectors making a 3 dimensional coordinate space can be defined. In certain embodiments this concept can be enhanced by head symmetries)).

Figure 7:
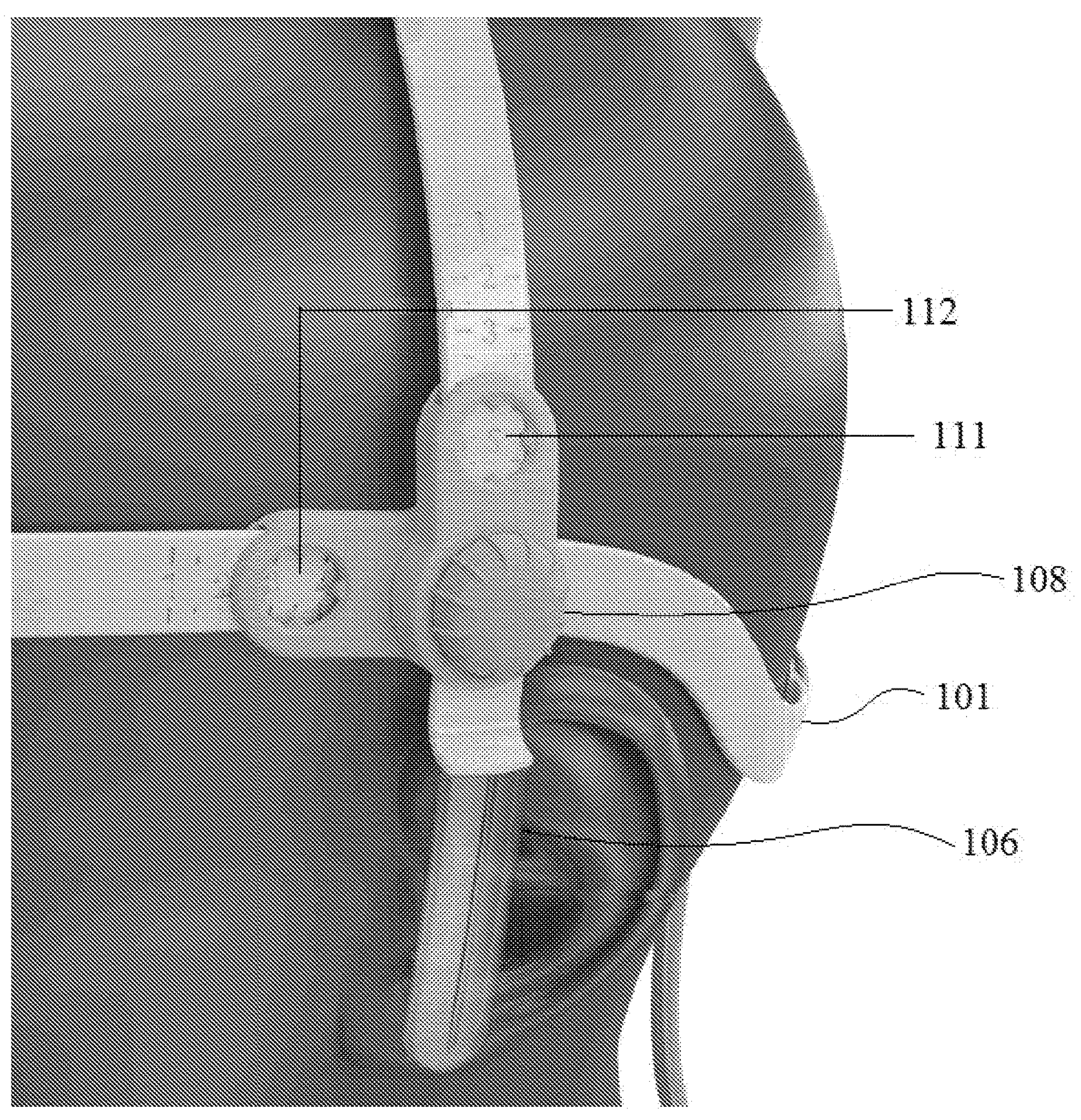
FIG. 7 is a magnified view of the embodiment of the apparatus shown in FIG. 1, showing the adjustability of the apparatus and the locking mechanism.

As shown ins FIG. 1-3, the headpiece 101 is adjustable in a plurality of different directions. The adjustability allows the anatomical markers to be aligned with their designated anatomical structures. Alignment of the anatomical markers with their anatomical structures automatically positions the stimulation sources, e.g., energy sources 103 and 104, to produce energy fields that intersect each other at a target neural tissue inside the head, i.e., beneath the scalp. Headpiece 101 typically includes at least one point of adjustability. However, headpiece 101 may have more than one point of adjustability, for example, two, three, four, five, six, seven, eight, nine, or ten points of adjustability, so that headpiece 101 can be adjustable in a plurality of different directions. Apparatus 100 as shown in FIGS. 1-3 includes a headpiece 101 that has four points of adjustability. There is adjustability at the top of the headpiece 101, at the side of headpiece 101, and at the back of headpiece 101. Those points of adjustability are only exemplary, and the invention contemplates that the adjustability point or points can be located anywhere along the headpiece. Generally, the adjustability will be in at least one direction, e.g., vertical, horizontal, diagonal, forward, backward, etc. Headpiece 101 is adjustable in both the vertical and horizontal directions. FIG. 7 shows a magnified view of the adjustability of the apparatus 100. As shown in FIG. 7, each point of adjustability includes measurement markers so that the settings of the headpiece 101 can be recorded and for later use, such as to reproduce exact stimulation source placement on a patient's head. The measurement markers can be in any unit of measurement, such as centimeters or millimeters. Each point of adjustability includes measurement markers. FIG. 7 shows the intersection of two points of adjustability, a vertical adjustment 111 and a horizontal adjustment 112. The point of adjustment on the rear of the headpiece 101 only has horizontal adjustment. The point of adjustment on the top of headpiece 101 only has forward and backward adjustment. In alternative embodiments the system can also have further points of adjustment, for example in and apparatus described by FIGS. 1, 3, and 4 there are six points of adjustment, including a horizontal and vertical adjustment on the both sides of the apparatus above two different tragus locators (FIGS. 1 and 4), one on the top of the headpiece for forward and backward adjustment, and one on the rear of the headpiece for horizontal adjustment. In alternative embodiments, the measurement marker(s) and point(s) of adjustment can be separate components. In alternative embodiments measurement marker(s) can also be integrated into other parts of the device, such as along the micro adjust ball joint 103*c* or on the face of the receptacle 103, to allow for measurement of the micro adjust ball joint, such as in displaying the relative angles and/or depth of the ball joint. In alternative embodiments the measurements can be completed, assisted, and/or automated by transduction mechanisms and/or integrated circuits, which could be internally housed, and/or coupled to the system through a telecommunications device. The transduction mechanisms could be used to make any type of assessment such as for example to assess distance, position, angle, distance, altitude, acceleration, gyroscopic information, velocity, pressure, temperature, force, and/or tightness.

In certain embodiments, each point of adjustability may include a locking mechanism. However, if two points of adjustability intersect, a single locking mechanism can function to lock both of those points of adjustability. Once the proper alignment is achieved, the configuration of the headpiece is locked in place. Accordingly, the apparatus is customized to a subject's head and repeatably and reliably positions a non-invasive stimulation source at a proper location on the subject's head for stimulation of a particular brain structure. In that manner, a subject does not need to be re-measured for each stimulation session, because the apparatus has been custom fit to the user's head. That saves the subject time during subsequent stimulation sessions and the reproducibility of the targeting makes it easy to effectively dose the stimulation and characterize safety parameters. Furthermore, once custom fit, imaging data is not required for positioning of the stimulation source in subsequent stimulation sessions, so the subject can receive stimulation outside of a physician's office. Furthermore, in certain embodiments, imaging data is not needed and stimulation to certain brain areas can be determined based on customizing the fits of the device to the patient (such as for example providing anodal tDCS to a patient's primary motor cortex while fixing the cathode above the contralateral orbital).

In other embodiments, there is no locking mechanism because it is an optional component of the apparatuses of the invention. That is, apparatuses of the invention can function without the locking mechanism, but such embodiments require that a technician or user to check the apparatus to ensure that the stimulation sources are properly aligned prior to their use.

FIGS. 1-3 illustrate an embodiment that includes locking mechanisms 108, 109, and 110. Locking mechanism 108 controls locking of vertical adjustment 111 and horizontal adjustment 112 on the headpiece 101, more clearly seen in the magnified view of FIG. 7. Locking mechanism 109 controls locking of the point of adjustability at the top of the headpiece 101. Locking mechanism 110 controls locking of the point of adjustability at the rear of the headpiece 101. Any locking mechanism known in the art that secures the adjustability of the headpiece 101 so that its configuration is locked into an unmovable and fixed configuration can be used with apparatuses of the invention. The exemplary locking mechanism shown in FIGS. 1-3 is a tightening wheel for each of locking mechanisms 108, 109, and 110. Loosening the wheel, unlocks the locking mechanisms 108, 109, and 110, allowing for adjustability of the headpiece 101 in one or more directions. Tightening of the wheel locks the locking mechanism 108, 109, and 110, securing the adjustability of the headpiece 101 so that its configuration is locked into an unmovable and fixed configuration. While apparatus 100 is shown with three of the same locking mechanisms, that is not required, and each point of adjustability can use a different type of locking mechanism. In FIGS. 1, 3, and 4 an alternate embodiment is shown with a second tragus marker, where locking mechanisms are shown at 108, 109, 110, and 120. In FIGS. 1, 3, and 6 an alternative embodiment is shown including locking mechanisms at 108, 109, 110, and 120. In certain embodiments, the system could include an automated or electronically controlled locking mechanism(s).

In certain embodiments, imaging may be used to guide fine tuning of adjustability of the headpiece prior to it being locked into a fixed configuration, to assess the use of the device after it is locked into place during the time when it is being used, and/or to assess the use of the device after it is locked into place and after it has been used. Imaging to guide placement of stimulation/energy sources on a head is described for example in, Wagner et al., (U.S. patent application publication number 2011/0275927), the content of which is incorporated by reference herein in its entirety.

In other embodiments, the filtering properties of the neural tissue within the head are used to guide fine tuning of adjustability of the headpiece prior it being locked into a fixed configuration, which can be optionally done in conjunction with imaging. Calculating and tuning stimulation based on filtering properties (e.g., mechanical and/or electrical filtering properties) of tissue is described for example, Wagner et al., (U.S. patent application publication number 2012/0226200), the content of which is incorporated by reference herein in its entirety.

Figure 10:
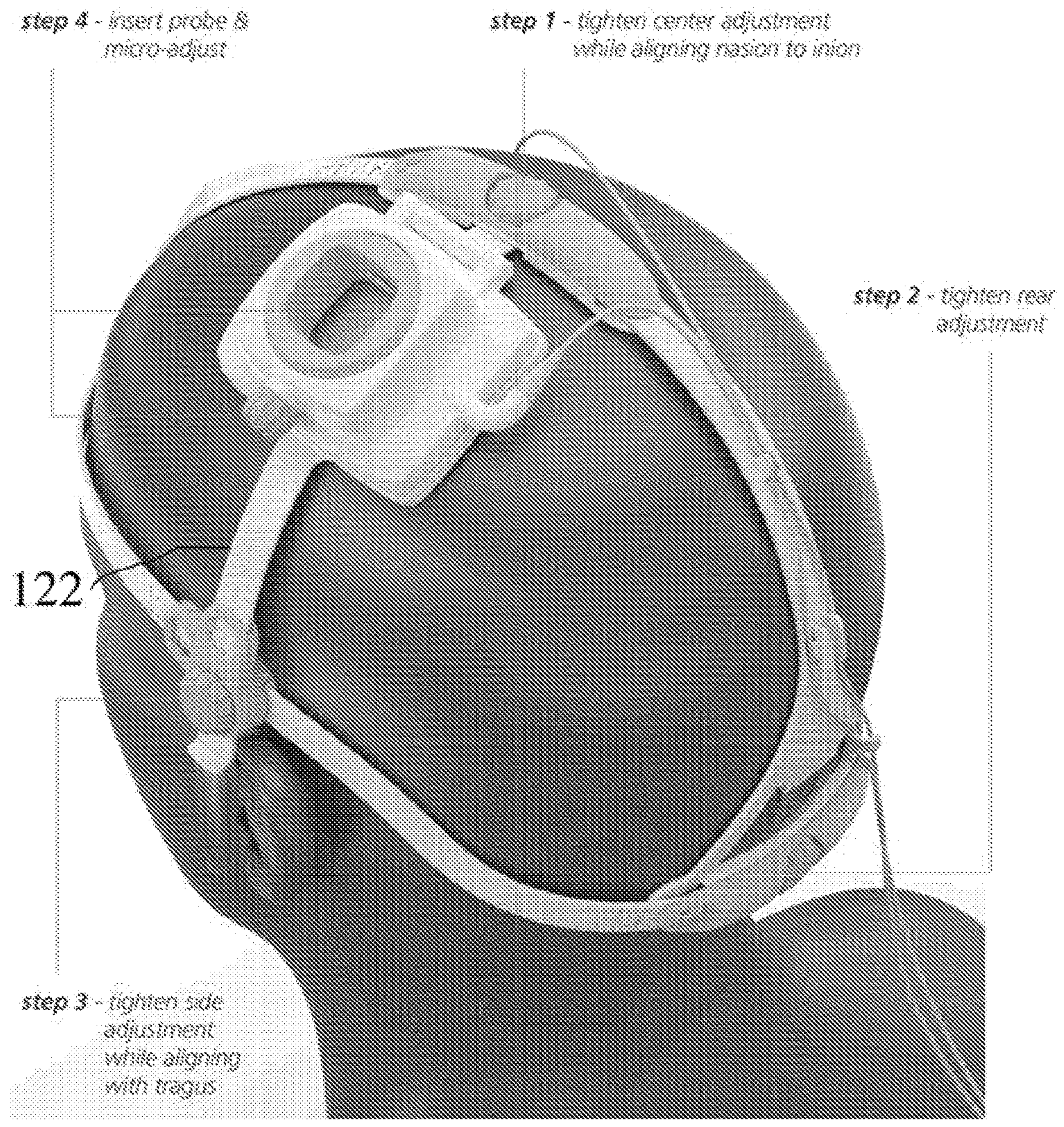
FIG. 10 illustrates a method for using apparatuses of the invention.

FIG. 10 illustrates a method for using apparatuses of the invention. Apparatus 100 is placed on a head of a user. In Step 1, the center component of the headpiece that traverses along a top of the head is adjusted so that the nasion marker aligns with the nasion of the user and the inion marker aligns with the inion of the user. Once aligned, the measurement on the top adjustment point is recorded and the top center adjustment point is tightened and locked into position. This point allows one to localize a location along the line between the inion and nasion. In Step 2, the measurement on the rear adjustment point is recorded and the rear adjustment point is tightened and locked into position. In Step 3, the side component of the headpiece that traverses along a side of the head is adjusted so that the tragus marker aligns with the tragus of the user, for example here on a point of the posterior root of the zygomatic arch lying immediately in front of the upper end of the tragus. That adjustment may involves both horizontal and vertical adjustments, so that the system is correctly placed relative to the tragus. In the embodiment shown, the system makes use of the symmetry of the head, and the relative fixed position of the headpiece components along the opposite side of the head, to assure that the band 122 is placed along the coronal plane containing the tragus of both the left and right ears and the midpoint between the inion and nasion (i.e., the midpoint intersection along the line on the scalp between the inion and nasion and the midpoint intersection along the line on the scalp between left tragus to right tragus are in this plane). During this positioning step, the receptacle 103, which contains the stimulation sources is placed to the desired location, such as for example moving the receptacle approximately 20% (or approximately 5 cm for typical head sizes) from the vertex of the head along the line established under the band 122, which runs along the plane from left tragus to right tragus and contains the CZ (located in steps 1 and 2); thereby localizing the motor cortex. Once aligned, the horizontal and/or vertical measurements on the side adjustment point are recorded and the side adjustment point is tightened and locked into position. Once the proper alignment is achieved, the configuration of the headpiece is locked in place. In Step 4, the ultrasound probe is coupled to the receptacle 103 and a micro-adjust is performed if necessary. At that point, the user is ready to receive stimulation. Accordingly, the apparatus is customized to a subject's head and repeatably and reliably positions a non-invasive stimulation source at a proper location on the subject's head for stimulation of a particular brain structure. In that manner, a subject does not need to be re-measured for each stimulation session, because the apparatus has been custom fit to the user's head. That saves the subject time during subsequent stimulation sessions and the reproducibility of the targeting makes it easy to effectively dose the stimulation and characterize safety parameters. Furthermore, once custom fit, imaging data is not required for positioning of the stimulation source in subsequent stimulation sessions, so for example the subject can receive stimulation outside of a physician's office. Additionally, targeting via this method can be done without any imaging for cortical and sub-cortical target locations depending on the stimulation source implemented and desired target(s).

In other embodiments, the device can be coupled to a source or sources that provide sensory signals to the wearer, such as devices which provide visual, auditory, tactile, smell, and/or taste stimuli, for example the device might simply be coupled to a light source, which for example could provide a light signal to a patient (such as certain light to sooth the patient during stimulation), or coupled to a sound source which provides a signal to adjust the level of alertness of a patient, or coupled to multiple sensory information such as a virtual reality system.

While as described above, any material which is safe and efficacious can be used for the design of the headpiece, in alternative embodiments the device could be designed entirely out of materials compatible with imaging systems (such MRI compatible materials and/or materials compatible with imaging systems described in Wagner et al. (U.S. patent application publication number 2011/0275927)). This would allow one to wear the device during imaging, whether for stimulation while undergoing imaging or to simply analyze the imaging data with the headpiece in place (even when stimulation is not being given). The headpiece could also be integrated with registration/marker materials (such as for example vitamin E pellets for MRI, air filled tubes for MRI, metallic pellets for MRI, metallic pellets for CT, Gallium-68 for PET, Co-57 for SPECT, etc.) to be able to localize the relative location of the headpiece and stimulation sources to head and/or brain targets. The headpiece can also be coupled with other physiological measurement methods, such as those described in described in Wagner et al. (U.S. patent application publication number 2011/0275927). When both recording (imaging and/or physiological measurement methods) and stimulation systems are used, the recording and stimulation systems could be coupled, such as through an analysis circuit or computational system, to provide further control of stimulation or to focus the recording system. The coupling circuit and/or analysis circuit could be housed in one of the receptacles or in a component of the headpiece.

The device can be designed using mechanical hand-operated parts and/or developed with automation technology, such as with control circuitry, robotic components, and/or transduction mechanisms. These components can be used to control any part of the device use, from placement to relative measurements between different anatomical markers.

In alternative embodiments the system can be designed so all or part of the stimulation source power components and control electronics are housed in the receptacles or other parts of the headpiece, so there is no need for wire connectivity, and or the device could be worn while moving and/or performing other activities which would be prevented from having external wired connections. A control system could further be connected to the system through a telecommunications device, such as for Bluetooth or wi-fi control (such as through a cell phone or personal computer device), such as described above. In certain embodiments, computational components, power components, storage, read, and/or write circuitry can be integrated into the device.

In certain embodiments, the headpiece can make use of a component(s) which combines a receptacle(s) and anatomical marker(s) such that they are not separate in form and/or function or that they housed together in a similar coupling structure, such as for example stimulation can take place at one of the anatomical marker points as might be the case for an occipital lobe directed stimulation placed from an inion point.

Figure 11:
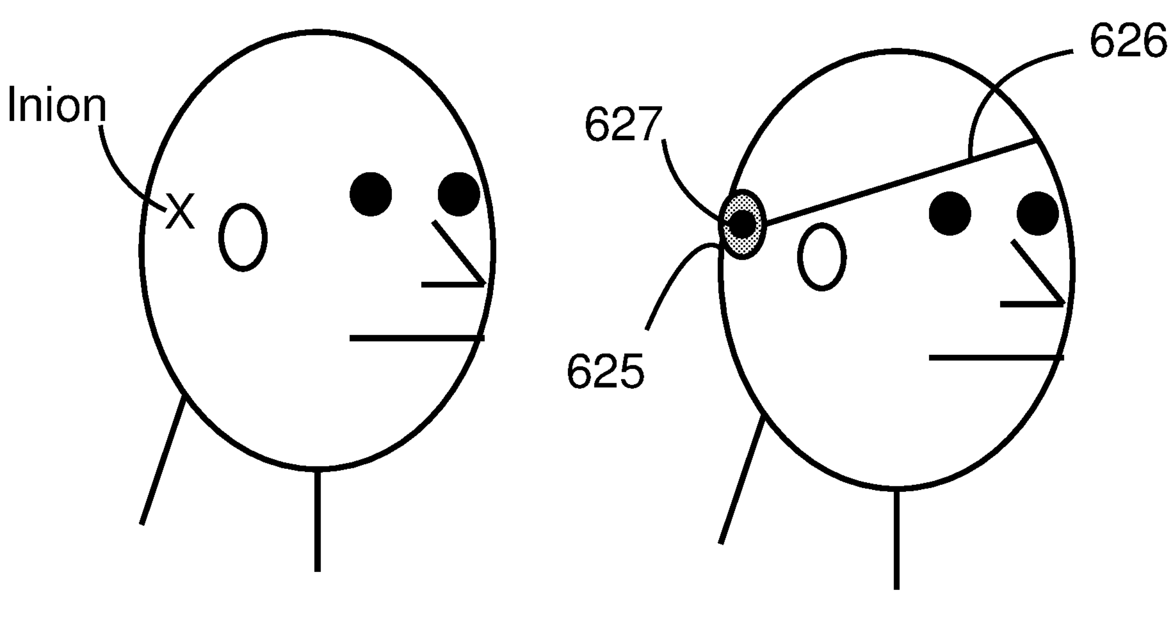
FIG. 11 is an illustration of an embodiment of an apparatus of the invention using a single anatomical marker and a single stimulation source.

As already mentioned, the above is an exemplary embodiment of the invention. FIG. 11 shows another embodiment of the invention. This embodiment provides an apparatus having a headpiece configured to be worn on a head of a user. The headpiece includes a single receptacle configured to receive and retain an energy source. The headpiece is adjustable in at least one direction. There is at least one anatomical marker coupled to the headpiece so that a position of the receptacle can be adjustably aligned to a region of neural tissue in the head based on an alignment of the at least one anatomical marker with its designated anatomical structure. Specifically in FIG. 11, an anatomical marker 625 is placed on the inion of the subject, the marker is a circular ring shaped symmetrical marker with a hollow center aperture such that the operator can feel the inion centered inside the anatomical marker. An adjustable band 626 holds the marker and apparatus to the head, which can be attached while the operator keeps the aperture of the anatomical marker fixed on inion. A stimulator receptacle is then fixed to the anatomical marker such that it can make contact with the scalp surface through the aperture on the anatomical marker 625 (for example such the bridging medium of the receptacle is localized in the center of the aperture) and provide a stimulation to neural tissue targeted in the vicinity of the electrode, such as nearby occipital lobe tissue. Single anatomical markers limit stimulation to locations in the vicinity of the marker with targeted focal stimulation, but with broad stimulation the anatomical marker can serve as a reference for even targets not in the immediate vicinity of the anatomical marker and or stimulation source which may or may not be integrated with the anatomical marker.

Figure 12:
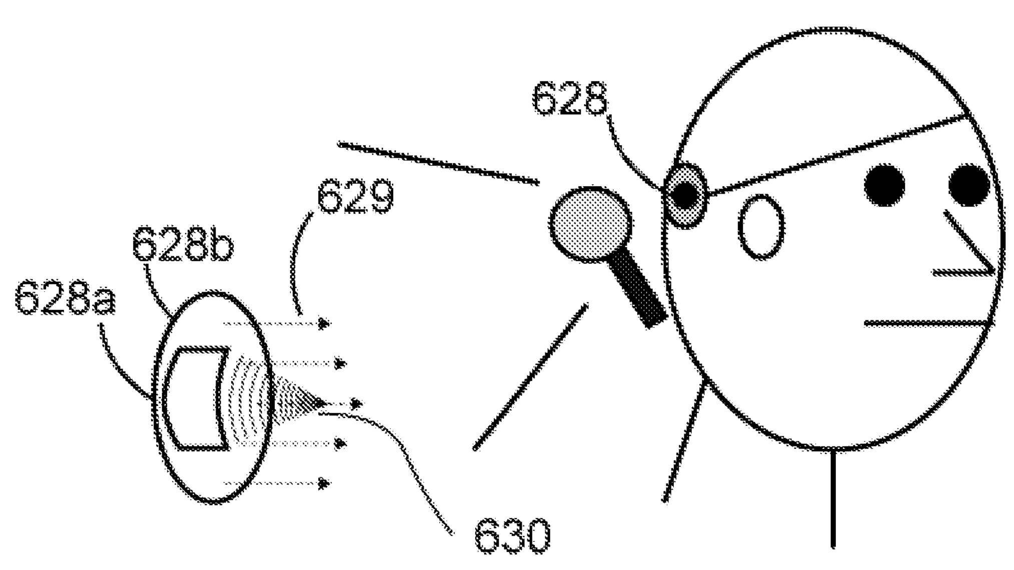
FIG. 12 is an illustration of an embodiment of an apparatus of the invention using a single anatomical marker and two stimulation source.
Figure 13:
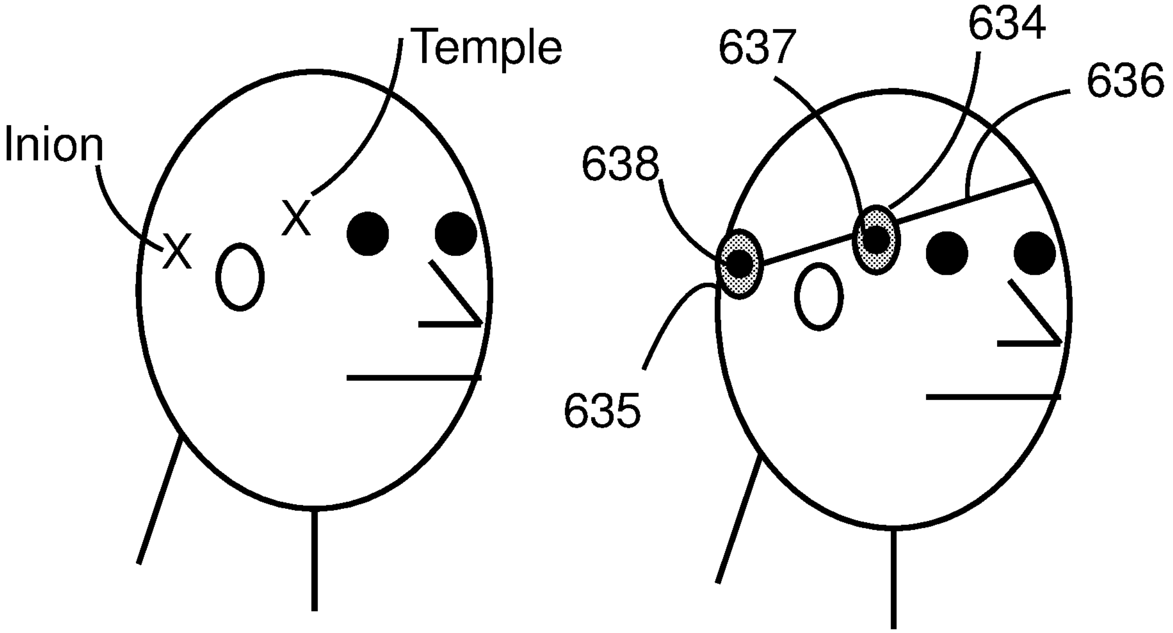
FIG. 13. is an illustration of an embodiment of an apparatus of the invention using two anatomical markers and two stimulation sources.

FIG. 12 is another embodiment of the invention, showing an apparatus with two stimulation sources and 1 marker, which is similar to the apparatus in FIG. 11 but the receptacle contains a first stimulation source 628*a* (herein by example an electrical source) and a second stimulation source 628*b* (herein by example an ultrasound source), which generates both an electric field 629 and sonic field 630. It is shown by example with multiple sources in the same receptacle, however alternate embodiments are envisioned with multiple receptacles. FIG. 13 shows an embodiment that uses two stimulation sources and two anatomical markers, where the temple and the inion are located with anatomical markers 634 and 635 respectively, a band 636 holds the system in place, and two separate receptacles 637 and 638 are placed to hold and interface the stimulation sources.

While the device is preferably designed to be used with human subjects, alternative embodiments entail adapting the technology for other species, e.g., other primates, such as monkeys.

In alternative embodiments, a headpiece could be worn to allow for pre-surgical evaluation prior to deep brain stimulation surgery. For example, by wearing the headpiece and allowing an operator to adjust the positioning of the stimulator until a patient maintains an ideal and/or improved response to stimulation, the headpiece could be used in helping identify the proper brain stimulation targets.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. An apparatus comprising:
- a headpiece configured to be worn on a head of a user and comprising at least a first single receptacle configured to receive and retain both a first energy source and a first portion of a second energy source therein, wherein the first energy source is transcranial ultrasound (TUS) and the second energy source is transcranial direct current stimulation (TDCS);
- a U-shaped bridging medium at least partially disposed within the first single receptacle and aligned with the first portion of the second energy source;
- at least one adjustment mechanism disposed on the headpiece and configured to move the first single receptacle within a 3 dimensional space about the user's head; and
- at least one marker physically coupled to the headpiece and configured to be aligned with at least one anatomical structure of the user's head, wherein a position of the first energy source can be adjustably aligned to a target region of neural tissue in the user's head by aligning the at least one marker with its designated anatomical structure with at least one of the plurality of adjustment mechanisms.

2. The apparatus according to claim 1, further comprising the first energy source and the portion of the second energy source.

3. The apparatus according to claim 1, wherein at least two markers are arranged about the headpiece to be perpendicular to each other.

4. The apparatus according to claim 1, wherein at least two markers are arranged about the headpiece to be 180 degrees with respect to each other.

5. The apparatus according to claim 1, wherein the headpiece further comprises a second receptacle configured to receive and retain a second portion of the second energy source.

6. The apparatus according to claim 1, wherein the first single receptacle comprises a safety component operably coupled to the first energy source and the first portion of the second energy source, wherein the safety component is configured to render the first and second energy sources inoperable based on a measured characteristic of a stimulation delivered by the first energy source, the second energy source, or both.

7. The apparatus according to claim 6, wherein the measured characteristic comprises at least one of stimulation intensity, stimulation duration, temperature, conductivity, a property of the U-shaped bridging medium, a property of the user's scalp, or a property of a connection between the first and second energy sources and the user's scalp.

8. The apparatus according to claim 1, further comprising a transduction mechanism configured to assess a characteristic of the apparatus and control any part of the apparatus.

9. The apparatus according to claim 1, further comprising a second bridging medium disposed within the first single receptacle, wherein the second bridging medium is aligned with the first energy source.

10. An apparatus comprising:

a headpiece configured to be worn on a head of a user and comprising a first single receptacle configured to receive and retain both a first energy source and a first portion of a second energy source therein and a second receptacle configured to receive and retain a second portion of the second energy source;

a U-shaped bridging medium at least partially disposed within the first single receptacle and aligned with the first portion of the second energy source;

an adjustment mechanism disposed on the headpiece and configured to move at least one of the first single receptacle or the second receptacle within a 3 dimensional space about the user's head; and at least three markers, each marker being physically coupled to the headpiece and configured to be aligned with at least one anatomical structure of the user's head, wherein a first marker is a nasion marker, a second marker is an inion marker, and a third marker is a first tragus marker, and wherein the apparatus is configured so that a position of at least one of the first energy source or the second energy source can be adjustably aligned relative to a target region of neural tissue in the user's head by aligning the at least three markers with their designated anatomical structures with the adjustment mechanism.

11. The apparatus according to claim 10, wherein the position of the first energy source receptacle is adjustable and the position of the second energy source receptacle is fixed.

12. The apparatus according to claim 10, further comprising a fourth marker and wherein the fourth marker is a second tragus marker.

13. The apparatus according to claim 12, wherein the first tragus marker aligns to one side of the head and the second tragus marker aligns to the other side of the head.

14. The apparatus according to claim 10, wherein alignment of at least two of the markers with their designated anatomical structures automatically orients the first single receptacle relative to the second receptacle so that energy fields produced by the first energy source and the second energy source intersect each other at the target region of neural tissue.

15. The apparatus according to claim 10, wherein the first portion of the second energy source comprises a cathode and the second portion of the second energy source comprises an anode, wherein alignment of the first and second receptacles comprises aligning the second portion of the second energy source with the user's primary motor cortex while fixing the first portion of the second energy source above the contralateral orbital.

16. An apparatus comprising:

a headpiece configured to be worn on a head of a user and comprising at least a first receptacle configured to receive and retain a first energy source;

a U-shaped bridging medium at least partially disposed within the first receptacle;

at least one adjustment mechanism disposed on the headpiece and configured to move the first receptacle within a 3 dimensional space about the user's head;

at least one marker coupled to the headpiece and configured to be aligned with at least one anatomical structure of the user's head, wherein a position of the first energy source can be adjustably aligned to a target region of neural tissue in the user's head by aligning the at least one marker with its designated anatomical structure with the at least one adjustment mechanism; and a transduction mechanism configured to assess a characteristic of the apparatus and control any part of the apparatus.

17. The apparatus according to claim 16, wherein the first energy source comprises at least one of a mechanical source, an electrical source, a magnetic source, an optical source, a thermal source, Transcranial Direct Current Stimulation (TDCS), Transcranial Ultrasound (TUS), Transcranial Doppler Ultrasound (TDUS), Transcranial Electrical Stimulation (TES), Transcranial Alternating Current Stimulation (TACS), Cranial Electrical Stimulation (CES), Transcranial Magnetic Stimulation (TMS) or combinations thereof.

18. The apparatus according to claim 16, further comprising a locking mechanism that locks adjustability of the headpiece to prevent further adjustment of the headpiece while the apparatus is being worn on the head of the user.

19. The apparatus according to claim 16, wherein the first energy source receptacle comprises a ball joint configured to provide micro-adjustment to the first energy source receptacle.

20. The apparatus of claim 16, wherein the transduction mechanism is configured to assess at least one of distance, position, angle, altitude, acceleration, gyroscopic information, velocity, pressure, temperature, force, and/or tightness of any part of the apparatus.

21. The apparatus of claim 16, wherein the transduction mechanism is configured to control placement of the first energy source.

* * * * *